United States Patent
Bourrie et al.

(10) Patent No.: US 6,967,203 B2
(45) Date of Patent: Nov. 22, 2005

(54) USE OF PYRIDOINDOLONE DERIVATIVES FOR PREPARING ANTICANCER MEDICINES

(75) Inventors: Bernard Bourrie, Saint-Gely-du-Fesc (FR); Pierre Casellas, Montpellier (FR); Jean-Marie Derocq, Murviel-les-Montpellier (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 10/476,322

(22) PCT Filed: Apr. 26, 2002

(86) PCT No.: PCT/FR02/01449

§ 371 (c)(1),
(2), (4) Date: Oct. 27, 2003

(87) PCT Pub. No.: WO02/087574

PCT Pub. Date: Nov. 7, 2002

(65) Prior Publication Data

US 2004/0122027 A1 Jun. 24, 2004

(30) Foreign Application Priority Data

Apr. 27, 2001 (FR) .............................. 01 05843

(51) Int. Cl.⁷ ............................................... A61K 31/44
(52) U.S. Cl. ....................................... 514/257; 514/292
(58) Field of Search .................................. 514/292, 257

(56) References Cited

U.S. PATENT DOCUMENTS 4,263,304 A * 4/1981 Ishizumi et al. ............ 414/262
4,835,160 A   5/1989 Bisagni et al.
5,880,126 A   3/1999 Skuballa et al.

FOREIGN PATENT DOCUMENTS

| FR | 2003999 | 11/1969 |
| FR | 2765581 | 1/1999 |
| WO | WO 9951597 | 10/1999 |

OTHER PUBLICATIONS

Cecil, Textbook of Medicine, Goldman et al., eds., 21$^{st}$ ed., vol. 1, published 2000 by W.B. Saunders Co. (PA), pp 1060–74.*
Derwent Patent Abstract No. 196800 (2003).
Derwent Patent Abstract No. 199909 (2003).
Derwent Abstract No. 198213 (1982).

* cited by examiner

*Primary Examiner*—Raymond J. Henley, III
(74) *Attorney, Agent, or Firm*—M. D. Alexander; Kelly Bender; Paul Darkes

(57) ABSTRACT

The invention relates to a novel use of compounds of formula:

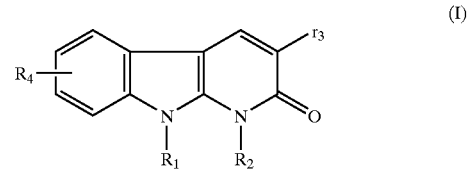

(I)

for the preparation of medicinal products that are useful as anticancer agents.

10 Claims, No Drawings

USE OF PYRIDOINDOLONE DERIVATIVES FOR PREPARING ANTICANCER MEDICINES

The present invention relates to a novel therapeutic application of pyridoindolone derivatives.

The document FR 97/08409 describes compounds of formula:

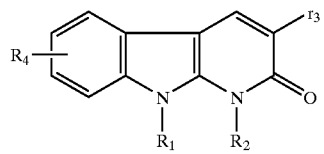

(I)

in which:
R$_1$ represents a hydrogen atom or a methyl or ethyl group;
R$_2$ represents a methyl or ethyl group; or
R$_1$ and R$_2$ together form a (CH$_2$)$_3$ group;
r$_3$ represents either a phenyl group optionally substituted with a halogen atom or a methyl or methoxy group, or a thienyl group;
R$_4$ represents a hydrogen or chlorine atom or a methyl or methoxy group.

In the description of the said document, it is mentioned that the compounds of formula (I) that have affinity for the omega modulatory sites associated with the GABA$_A$ receptors can be used in the treatment of complaints linked to gabaergic transmission disorders associated with the GABA$_A$ receptor subtypes, such as anxiety, sleeping disorders, epilepsy, etc.

It has now been found that the compounds of formula (I) are anticancer agents that inhibit the proliferation of tumor cells and that have antimitotic properties.

The invention relates to the use of the compounds of formula (I) as defined above, and of the pharmaceutically acceptable salts, hydrates or solvates thereof, for the preparation of medicinal products that are useful as anticancer agents.

Preferred compounds according to the invention are the compounds of formula:

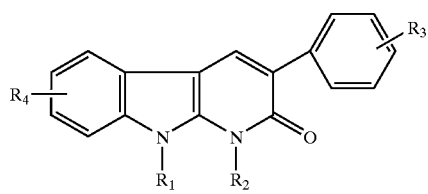

(Ia)

in which:
R$_1$ represents a hydrogen atom or a methyl or ethyl group;
R$_2$ represents a methyl or ethyl group; or
R$_1$ and R$_2$ together form a (CH$_2$)$_3$ group;
R$_3$ represents a hydrogen or halogen atom or a methyl or methoxy group;
R$_4$ represents a hydrogen or chlorine atom or a methyl or methoxy group.

Particularly preferred compounds according to the invention are the compounds of formula:

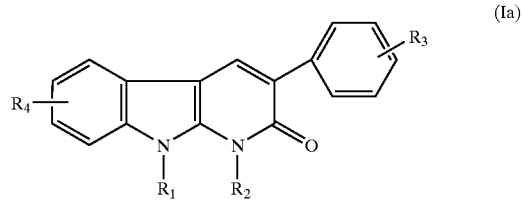

(Ia)

in which:
R$_1$ represents a hydrogen atom or a methyl or ethyl group;
R$_2$ represents a methyl or ethyl group;
R$_3$ represents a hydrogen or halogen atom or a methyl or methoxy group;
R$_4$ represents a hydrogen or chlorine atom or a methyl or methoxy group.

More particularly preferred compounds according to the invention are the compounds of formula:

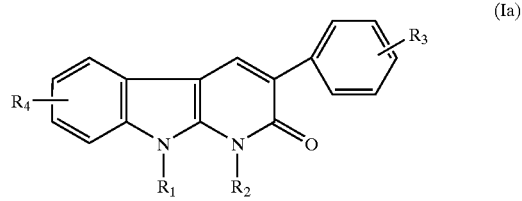

(Ia)

in which:
R$_1$ represents a methyl or ethyl group;
R$_2$ represents a methyl or ethyl group;
R$_3$ represents a hydrogen or halogen atom or a methyl or methoxy group;
R$_4$ represents a hydrogen or chlorine atom or a methyl or methoxy group.

By way of example, compounds of the invention are the following:
6-chloro-1,9-dimethyl-3-phenyl-1,9-dihydro-2H-pyrido[2,3-b]indol-2-one; m.p.=178.5–179.5° C.;
3-(4-methoxyphenyl)-1,9-dimethyl-1,9-dihydro-2H-pyrido[2,3-b]indol-2-one; m.p. 166–167° C.;
1,6,9-trimethyl-3-(3-thienyl)-1,9-dihydro-2H-pyrido[2,3-b]indol-2-one;
NMR (200 MHz): 2.6 ppm: s: 3H; 4.1 ppm: s: 3H; 4.2 ppm: s: 3H; 7.1 ppm: d: 1H; 7.4–7.9 ppm: m: 4H; 8.3 ppm: d: 1H; 8.7 ppm: s: 1H;
1,6,9-trimethyl-3-phenyl-1,9-dihydro-2H-pyrido[2,3-b]indol-2-one; m.p.=198–199° C.;
1,6-dimethyl-3-phenyl-1,9-dihydro-2H-pyrido[2,3-b]indol-2-one;
NMR (200 MHz): 2.5 ppm: s: 3H; 3.8 ppm: s: 3H; 7.1 ppm: d: 1H; 7.3–7.5 ppm: m: 4H; 7.75 ppm: d: 2H; 7.8 ppm: s: 1H; 8.4 ppm: s: 1H; 11.8 ppm: s: 1H.

The compounds of formula (I) are prepared according to the process described in the document FR 97 08409.

The compounds of formula (I) according to the present invention were tested in vitro on a human breast cancer cell line: the line MDA-MB-231 available from the American Type Culture Collection (reference HTB26).

The assessment of the antiproliferative effect is carried out according to J. M. Derocq et al., FEBS Letters, 1998, 425, 419–425: the degree of incorporation of [3H]thymidine into the DNA of the treated cells is measured, after 96 hours of incubation of a compound of formula (I). The 50% inhibitory concentration (IC$_{50}$) is defined as the concentration that inhibits the cellular proliferation by 50%.

The compounds according to the invention have an IC$_{50}$ value generally of less than 10 µM on the MDA-MB-231 line.

The compounds of formula (I) were also tested on another human breast cancer cell line, referred to as the multi-drug resistant MDR line and known as MDA-A$_1$. This line is described by E. Collomb, C. Dussert and P. M. Martin in Cytometry, 1991, 12(1), 15–25.

The term "multi-drug resistant" which qualifies this line means that the said line is generally relatively insensitive to the chemotherapy drugs commonly used and in particular to antimitotic agents of natural origin such as paclitaxel, vincristine and vinblastine.

The compounds according to the invention have an IC$_{50}$ value that is generally less than 10 µM on the multi-drug resistant line MDA-A$_1$.

Thus, according to the present invention, the compounds of formula (I) inhibit the proliferation of tumor cells, including the proliferation of cells showing multi-drug resistance.

Several compounds according to the invention were assessed in vivo on a model of xenografting of human tumors implanted subcutaneously onto SCID (Severe Combined Immuno Deficiency) immunodeficient mice.

The treatment of the animals with a compound according to the invention started 6 to 7 days after the implantation, when the tumor reached a tumoral mass of about 60 mg. The compound, as a solution in a solvent, was then administered orally.

The antitumor activity was assessed when the mean tumor mass reached about 1 000 mg in the control animals, treated with solvent alone: the T/C ratio was measured, T representing the mean weight of the tumors in the treated animals and C representing the mean weight of the tumors in the control animals. A T/C ratio of less than or equal to 42% is considered as indicating a significant antitumor activity according to Stuart T et al., in J. Med. Chem., 2001, 44 (11), 1758–1776. For an administered cumulative daily dose of between 50 and 300 mg/kg, certain compounds according to the invention gave a T/C ratio of less than 20%.

The compounds of formula (I), and the pharmaceutically acceptable salts, hydrates or solvates thereof, are useful for preventing or treating diseases caused or exacerbated by the proliferation of tumor cells, such as primary or metastatic tumors, carcinomas and cancers, in particular: breast cancer; lung cancer; cancer of the small intestine, cancer of the colon and of the rectum; cancer of the respiratory pathways, of the oropharynx and of the hypopharynx; cancer of the esophagus; liver cancer, stomach cancer, cancer of the bile ducts; cancer of the bile vesicle, cancer of the pancreas; cancers of the urinary pathways including the kidneys, the urothelium and the bladder; cancers of the female genital tract including cancer of the uterus, of the cervix and of the ovaries, chloriocarcinoma and trophoblastoma; cancers of the male genital tract including cancer of the prostate, of the seminal vesicles and of the testicles, and tumors of the germinal cells; cancers of the endocrine glands including cancer of the thyroid, of the pituitary and of the adrenal glands; skin cancers, including haemangiomas, melanomas and sarcomas, including Kaposi's sarcoma; tumors of the brain, of the nerves, of the eyes, of the meninges, including astrocytomas, gliomas, glioblastomas, retinoblastomas, neurinomas, neuroblastomas, schwannomas and meningiomas; tumors arising from hematopoietic malignant tumors including leukemias, chloromas, plasmacytomas, fungoid mycosis, lymphoma or T cell leukemia, non-Hodgkin lymphoma, malignant hemopathies and myelomas.

The compounds of formula (I) above may be used at daily doses of from 0.002 to 2 000 mg per kilogram of bodyweight of the mammal to be treated, preferably at daily doses of from 0.1 to 300 mg/kg. In man, the dose may preferably range from 0.02 to 10 000 mg per day and more particularly from 1 to 3 000 mg, depending on the age of the individual to be treated or the type of treatment (prophylactic or curative).

According to another of its aspects, the present invention relates to pharmaceutical compositions comprising, as active principle, an effective dose of at least one compound according to the invention, or a pharmaceutically acceptable salt, a hydrate or a solvate of the said compound, and also one or more pharmaceutically acceptable excipients.

The said excipients are chosen according to the pharmaceutical form and the desired mode of administration, from the usual excipients that are known in the prior art.

The pharmaceutical compositions of the present invention may be prepared for oral, sublingual, subcutaneous, intramuscular, intravenous, topical, local, intratracheal, intranasal, transdermal or rectal administration to man and animals for the prevention or treatment of the diseases above.

The suitable administration forms comprise oral forms such as tablets, soft or hard gel capsules, powders, granules and oral solutions or suspensions, forms for sublingual, buccal, intratracheal, intraocular or intranasal administration, for administration by inhalation, forms for topical, transdermal, subcutaneous, intramuscular or intravenous administration, forms for rectal administration, and implants. For topical application, the compounds according to the invention may be used in creams, gels, ointments or lotions.

According to the usual practice, the dosage that is suitable for each patient is determined by the doctor according to the mode of administration, the age, the weight and the response of the said patient.

What is claimed is:

1. A method of inhibiting the proliferation of breast tumor cells which comprises administering to a patient in need of such inhibition an effective amount of a compound of formula:

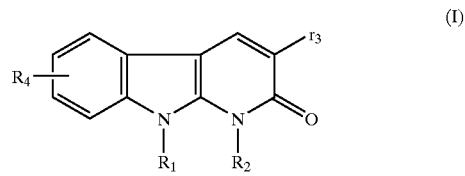

in which:

R$_1$ represents a hydrogen atom or a methyl or ethyl group;

R$_2$ represents a methyl or ethyl group; or

R$_1$ and R$_2$ together form a (CH$_2$)$_3$ group;

r$_3$ represents either a phenyl group optionally substituted with a halogen atom or a methyl or methoxy group, or a thienyl group;

R$_4$ represents a hydrogen or chlorine atom or a methyl or methoxy group; or a pharmaceutically acceptable salt thereof.

2. A method according to claim 1 which comprises administering a compound of formula:

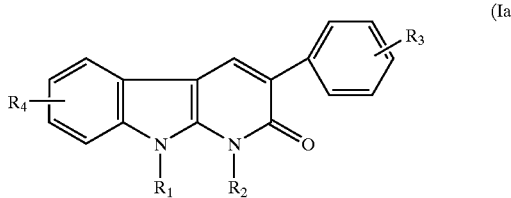

(Ia)

in which:
R₁ represents a hydrogen atom or a methyl or ethyl group;
R₂ represents a methyl or ethyl group; or
R₁ and R₂ together form a (CH₂)₃ group;
R₃ represents a hydrogen or halogen atom or a methyl or methoxy group;
R₄ represents a hydrogen or chlorine atom or a methyl or methoxy group; or a pharmaceutically acceptable salt thereof.

3. A method according to claim 1 which comprises administering a compound of formula:

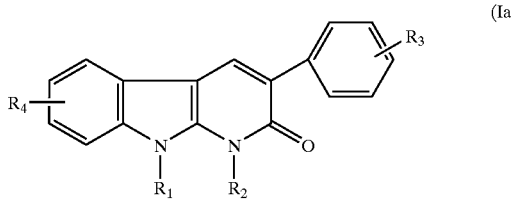

(Ia)

in which:
R₁ represents a hydrogen atom or a methyl or ethyl group;
R₂ represents a methyl or ethyl group;
R₃ represents a hydrogen or halogen atom or a methyl or methoxy group,
R₄ represents a hydrogen or chlorine atom or a methyl or methoxy group; or a pharmaceutically acceptable salt thereof.

4. A method according to claim 1 wherein the compound is selected from:
6-chloro-1,9-dimethyl-3-phenyl-1,9-dihydro-2H-pyrido[2,3-b]indol-2-one;
3-(4-methoxyphenyl)-1,9dimethyl-1,9dihydro-2H-pyrido[2,3-b]indol-2-one;
1,6,9-trimethyl-3-(3-thienyl)1,9-dihydro-2H-pyrido[2,3-b]indol-2-one;
1,6,9-trimethyl-3-phenyl-1,9dihydro-2H-pyrido[2,3-b]indol-2-one; or
1,6dimethyl-3-phenyl-1,9dihydro-2H-pyrido[2,3-b]indol-2-one; or a pharmaceutically acceptable salt thereof.

5. A method according to claim 1 which comprises administering a compound of formula:

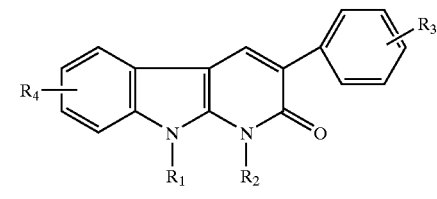

(Ia)

in which:
R₁ represents a methyl or ethyl group;
R₂ represents a methyl or ethyl group;
R₃ represents a hydrogen or halogen atom or a methyl or methoxy group;
R₄ represents a hydrogen or chlorine atom or a methyl or methoxy group; or a pharmaceutically acceptable salt thereof.

6. A method for treating breast cancer or breast tumors which comprises administering to a patient in need of such treatment an effective amount of a compound of formula:

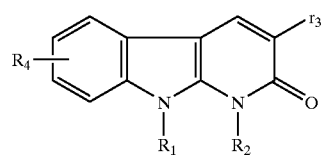

(I)

in which:
R₁ represents a hydrogen atom or a methyl or ethyl group;
R₂ represents a methyl or ethyl group; or
R₁ and R₂ together form a (CH₂)₃ group;
r₃ represents either a phenyl group optionally substituted with a halogen atom or a methyl or methoxy group, or a thienyl group;
R₄ represents a hydrogen or chlorine atom or a methyl or methoxy group; or a pharmaceutically acceptable salt thereof.

7. A method according to claim 6 which comprises administering a compound of formula:

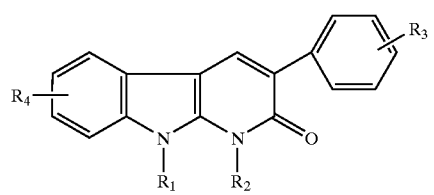

(Ia)

in which:
R₁ represents a hydrogen atom or a methyl or ethyl group;
R₂ represents a methyl or ethyl group; or
R₁ and R₂ together form a (CH₂)₃ group;
R₃ represents a hydrogen or halogen atom or a methyl or methoxy group;
R₄ represents a hydrogen or chlorine atom or a methyl or methoxy group; or a pharmaceutically acceptable salt thereof.

8. A method according to claim 6 which comprises administering a compound of formula:

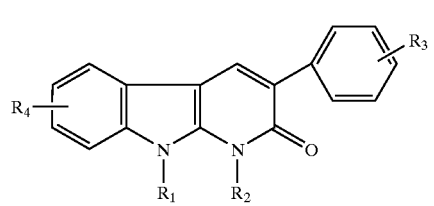

(Ia)

in which:
R₁ represents a hydrogen atom or a methyl or ethyl group;
R₂ represents a methyl or ethyl group;

R<sub>3</sub> represents a hydrogen or halogen atom or a methyl or methoxy group;

R<sub>4</sub> represents a hydrogen or chlorine atom or a methyl or methoxy group; or a pharmaceutically acceptable salt thereof.

9. A method according to claim 6 which comprises administering a compound of formula:

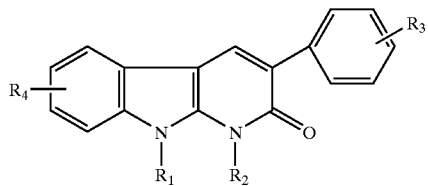

in which:

R<sub>1</sub> represents methyl or ethyl group;

R<sub>2</sub> represents a methyl or ethyl group;

R<sub>3</sub> represents a hydrogen or halogen atom or a methyl or methoxy group;

R<sub>4</sub> represents a hydrogen or chlorine atom or a methyl or methoxy group.

10. A method according to claim 6 wherein the compound is selected from:

6-chloro-1,9dimethyl-3-phenyl-1,9dihydro-2H-pyrido[2,3-b]indol-2-one;

3-(4-methoxyphenyl)-1,9-dimethyl-1,9dihydro-2H-pyrido[2,3-b]indol-2-one;

1,6,9-trimethyl-3-(3-thienyl)-1,9dihydro-2H-pyrido[2,3-b]indol-2-one;

1,6,9-trimethyl-3-phenyl-1,9-dihydro-2H-pyrido[2,3-b] indol-2-one; or 1,6-dimethyl-3-phenyl-1,9-dihydro-2H-pyrido[2,3-b] indol-2-one; or a pharmaceutically acceptable salt thereof.

* * * * *

UNITED STATES PATENT AND TRADEMARK OFFICE
CERTIFICATE OF CORRECTION

PATENT NO. : 6,967,203 B2  Page 1 of 1
APPLICATION NO. : 10/476322
DATED : November 22, 2005
INVENTOR(S) : Bourrie et al.

It is certified that error appears in the above-identified patent and that said Letters Patent is hereby corrected as shown below:

Claim 4, lines 45 to 46: "3-(4-methoxyphenyl)-1,9dimethyl-1,9dihydro-2H-pyrido[2,3-b]indol-2-one;" should read as -- 3-(4methoxyphenyl)-1,9-dimethyl-1,9dihydro-2H-pyrido[2,3-b]indol-2-one; --;

lines 47 to 48: "1,6,9-trimethyl-3-(3-thienyl)1,9-dihydro-2H-pyrido[2,3-b]indol-2-one;" should read as -- 1,6,9-trimethyl-3-(3-thienyl)-1,9-dihydro-2H-pyrido[2,3-b] indol-2-one; -- lines 49 to 50: "1,6,9-trimithyl-3-phenyl-1,9dihydro-2H-pyrido[2,3-b]indol-2-one; or" should read as -- 1,6.9-trimethyl-3-phenyl-1,9-dihydro-2H-pyrido[2,3-b]indol-2-one;or ; --;

lines 51 to 52: "1,6dimethyl-3-phenyl-1,9dihydro-2H-pyrido[2,3-b]indol-2-one;" should read as -- 1,6-dimethyl-3-phenyl-1,9-dihydro-2H-pyrido[2,3-b]indol-2-one; --

Claim 9, lines 3 to 4: "$R_4$ represents a hydrogen or chlorine atom or a methyl or methoxy group." should read as -- $R_4$ represents a hydrogen or chlorine atom or a methyl or methoxy group; or a pharmaceutically acceptable salt thereof. --

Claim 10, line 8 to 9: "6-chloro-1,9dimethyl-3-phenyl-1,9dihydro-2H-pyrido [2,3-b]indol-2-one;" should read as -- 6-chloro-1,9-dimethyl-3-phenyl-1,9-dihydro-2H-pyrido[2,3-b] indol-2-one; --;

lines 10 to 11: "3-(4-methoxyphenyl)-1,9-dimethyl-1,9dihydro-2H-pyrido[2,3-b]indol-2-one;" should read as -- 3-(4-methoxypenyl)-1,9-dimethyl-1-9-dihydro-2H-pyrido[2,3-b]indol-2-one; --;

Claim 10, lines 12 to 13: "1,6,9-trimethyl-3-(3-thienyl)-1,9dihydro-2H-pyrido [2,3-b]indol-2-one;" should read as -- 1,6,9-trimethyl-3-(3-thienyl)-1,9-dihydro-2H-pyrido[2,3-b]indol-2-one; --

Signed and Sealed this

Twenty-second Day of May, 2007

JON W. DUDAS
*Director of the United States Patent and Trademark Office*

UNITED STATES PATENT AND TRADEMARK OFFICE
CERTIFICATE OF CORRECTION

PATENT NO.         : 6,967,203 B2
APPLICATION NO.    : 10/476322
DATED              : November 22, 2005
INVENTOR(S)        : Bourrie et al.

It is certified that error appears in the above-identified patent and that said Letters Patent is hereby corrected as shown below:

Claim 10, lines 12 to 13: "1,6,9-trimethyl-3-(3-thienyl)-1,9dihydro-2H-pyrido[2,3-b]indol-2-onc;" should read as -- 1,6,9-trimethyl-3-(3-thienyl)-1,9-dihydro-2H-pyrido[2,3-b]indol-2-onc; --

Signed and Sealed this

Twelfth Day of June, 2007

JON W. DUDAS
*Director of the United States Patent and Trademark Office*